(12) United States Patent
Wang et al.

(10) Patent No.: US 8,667,832 B2
(45) Date of Patent: Mar. 11, 2014

(54) METHOD AND SYSTEM FOR PARTICLE SETTLING VELOCITY MEASUREMENT

(75) Inventors: Zhaowei Wang, Parma Heights, OH (US); Joanne M. Belovich, Hinckley, OH (US)

(73) Assignee: Cleveland State University, Cleveland, OH (US)

( * ) Notice: Subject to any disclaimer, the term of this patent is extended or adjusted under 35 U.S.C. 154(b) by 477 days.

(21) Appl. No.: 12/921,267

(22) PCT Filed: Mar. 4, 2009

(86) PCT No.: PCT/US2009/036031
§ 371 (c)(1),
(2), (4) Date: Nov. 15, 2010

(87) PCT Pub. No.: WO2009/111564
PCT Pub. Date: Sep. 11, 2009

(65) Prior Publication Data
US 2011/0048113 A1    Mar. 3, 2011

Related U.S. Application Data

(60) Provisional application No. 61/033,475, filed on Mar. 4, 2008.

(51) Int. Cl.
*G01N 15/04*    (2006.01)

(52) U.S. Cl.
USPC ........................................................ 73/61.65

(58) Field of Classification Search
USPC ............. 73/61.62, 61.63, 61.65, 61.68, 61.69
See application file for complete search history.

(56) References Cited

U.S. PATENT DOCUMENTS

| 3,199,775 A | | 8/1965 | Drucker |
| 3,660,037 A | * | 5/1972 | Sokol .............................. 422/73 |
| 4,419,879 A | | 12/1983 | Bush et al. |
| 4,710,874 A | * | 12/1987 | Cinqualbre ................... 356/442 |
| 4,794,789 A | | 1/1989 | Natako |

(Continued)

OTHER PUBLICATIONS

Robert H. Davis, Ching-Yuan Lee, Brian C. Batt, and Dhinakar S. Kompala, "Cell Separations Using Differential Sedimentation in Inclined Settlers," *Cell Separation Science and Technology*: developed from a symposium sponsored by the Divisions of Industrial and Engineering Chemistry, Inc., and Biochemical Technology, pp. 113-127, 1991 American Chemical Society.

(Continued)

*Primary Examiner* — John Fitzgerald
(74) *Attorney, Agent, or Firm* — Fay Sharpe LLP

(57) ABSTRACT

The invention provides a simple, inexpensive, accurate, and rapid method of measuring particle settling velocity comprising: (i) providing a gravity settler such as a column; (ii) filling the column with a first homogenous particle suspension, wherein the particle concentration in the first homogenous particle suspension is X, (iii) separating the column into an upper sub-column and a lower sub-column with a height h after settling the first homogenous particle suspension for a period of time t, wherein some particles remain in the upper sub-column; (iv) removing the particle suspension in the upper sub-column and mixing the particle suspension confined in the lower sub-column with a height h to prepare a second homogenous particle suspension; (v) measuring the particle concentration in the second homogenous particle suspension $X'$; and (vi) determining the particle settling velocity v with the formula: $v=h(X-X')/tX$. Also provided are device and system for carrying out the method.

20 Claims, 7 Drawing Sheets

(56) References Cited

U.S. PATENT DOCUMENTS

| | | | |
|---|---|---|---|
| 5,003,488 A * | 3/1991 | Hardy | 356/427 |
| 5,282,981 A * | 2/1994 | Adams et al. | 210/789 |
| 5,296,910 A | 3/1994 | Cole | |
| 5,594,164 A | 1/1997 | Bull | |
| 5,817,505 A | 10/1998 | Thompson et al. | |
| 5,875,899 A * | 3/1999 | Nishiyama | 209/156 |
| 6,202,855 B1 * | 3/2001 | Omtveit et al. | 209/172 |
| 6,308,434 B1 * | 10/2001 | Chickering et al. | 34/373 |
| 6,506,606 B1 | 1/2003 | Winkelman et al. | |
| 6,560,897 B2 * | 5/2003 | Chickering et al. | 34/577 |
| 7,732,725 B2 * | 6/2010 | Takagi et al. | 209/131 |
| 2003/0213729 A1 * | 11/2003 | Stencel et al. | 209/129 |
| 2007/0119754 A1 * | 5/2007 | Takagi et al. | 209/127.1 |
| 2011/0011776 A1 * | 1/2011 | Hongo et al. | 209/157 |
| 2011/0042279 A1 * | 2/2011 | Moriya et al. | 209/155 |

OTHER PUBLICATIONS

Linnie Rabjohn, DPM; Kevin Roberts, DPM, FACFAS, DABFAS; Michael Troiano, DPM; and Harold Schoenhaus, DPM, FACFAS, DABFAS, DABPO, "Diagnostic and Prognostic Value of Erythrocyte Sedimentation Rate in Contiguous Osteomyelitis of the Foot and Ankle," *The Journal of Foot & Ankle Surgery*, vol. 46, No. 4, Jul./Aug. 2007, pp. 230-237.

M. P. Dearnaley, "Direct Measurements of Settling Velocities in the Owen Tube: A Comparison with Gravimetric Analysis," *Journal of Sea Research* (*1996*), vol. 36 (1/2), pp. 41-47.

G. Erikssen, K. Liestøl, J. V. Bjørnholt, H. Stormorken, E. Thaulow and J. Erikssen, "Erythrocyte sedimentation rate: a possible marker of atherosclerosis and a strong predictor of coronary heart disease mortality," *European Heart Journal*, vol. 21, Issue 19, Oct. 2000, pp. 1614-1620.

N. B. Woodland, K. Cordatos, W. T. Hung, A. Reuben, and L. Holley, "Erythrocyte Sedimentation in Columns and the Significance of ESR," *Biorheology*, vol. 33, No. 6, pp. 477-488, 1996; 1997 Elsevier Science Ltd., printed in the USA.

Élisabeth Guazzelli, "Evolution of particle-velocity correlations in sedimentation," *Physics of Fluids*, vol. 13, No. 6, Jun. 2001, pp. 1537-1540, 2001 American Institute of Physics.

J. Lloyd Sutterby, "Falling Sphere Viscometry. I. Wall and Inertial Corrections to Stokes' Law in Long Tubes," *Transactions of the Society of Rheology*, vol. 17:4, pp. 559-573, The Society of Rheology, Inc. (1973), published by John Wiley & Sons, Inc.

Kirsten Wolfstein, "Fractionation and Measurements of Settling Velocities of Suspended Matter Using an Owen Tube," *Journal of Sea Research* (*1996*), vol. 36 (1/2), pp. 147-152.

Kelly K. Frame and Wei-Shou Hu, "Cell Volume Measurement as an Estimation of Mammalian Cell Biomass," *Biotechnology and Bioengineering*, vol. 36, pp. 191-197, (1990); published by John Wiley & Sons, Inc.

Chiou-Yu Choo, Yuan Tian, Wan-Seop Kim, Erich Blatter, Jon Conary, and Ciaran P. Brady, "High-Level Production of a Monoclonal Antibody in Murine Myeloma Cells by Perfusion Culture Using a Gravity Settler," *Biotechnol. Prog.* 2007, vol. 23, pp. 225-231; 2007 American Chemical Society and American Institute of Chemical Engineers, Published on Web Dec. 10, 2006.

B.S. Bull, M. Caswell, E. Ernst, J. M. Jou, A. Kallner, J. A. Koepke, S. M. Lewis, G. D. O. Lowe, M. W. Rampling and J. Stuart, "ICSH recommendations for measurement of erythrocyte sedimentation rate," *J. Clin. Pathol.* 1993, vol. 46, pp. 198-203.

Robert H. Perry and Don Green, *Perry's Chemical Engineers' Handbook*, Sixth Edition, published Jul. 2003, "Particle Dynamics," pp. 5-63-5-68.

Brian C. Batt, Robert H. Davis, and Dhinakar S. Kompala, "Inclined Sedimentation for Selective Retention of Viable Hybridomas in a Continuous Suspension Bioreactor," *Biotechnol. Prog.* 1990, vol. 6, pp. 458-464.

H. Mönig, D. Marquardt, T. Arendt and S. Kloehn, "Limited value of elevated erythrocyte sedimentation rate as an indicator of malignancy," *Family Practice*, vol. 19, No. 5, pp. 436-438, Oxford University Press 2002, printed in Great Britain.

P. N. Segrè, E. Herbolzheimer, and P. M. Chaikin, "Long-Range Correlations in Sedimentation," *Physical Review Letters*, vol. 79, No. 13, pp. 2574-2577, Sep. 29, 1997, The American Physical Society.

D. E. Martens, C. D. De Gooijer, C. A. M. Van Der Velden-De Groot, E. C. Beuvery, and J. Tramper, "Effect of Dilution Rate on Growth, Productivity, Cell Cycle and Size, and Shear Sensitivity of a Hybridoma Cell in a Continuous Culture," *Biotechnology and Bioengineering*, vol. 41, pp. 429-439, Feb. 20, 1993, John Wiley & Sons, Inc.

Nancy K. Goebel, Rod Kuehn and Michael C. Flickinger, "Methods for determination of growth-rate-dependent changes in hybridoma volume, shape and surface structure during continuous recycle," *Cytotechnology*, vol. 4, pp. 45-57, 1990, 1990 Kluwer Academic Publishers, printed in the Netherlands.

Shang-You Tee, P. J. Mucha, Luca Cipelletti, S. Manley, M. P. Brenner, P. N. Segre, and D. A. Weitz, "Nonuniversal Velocity Fluctuations of Sedimenting Particles," *Physical Review Letters*, vol. 89, No. 5, pp. 054501-1-054501-4, Jul. 29, 2002, The American Physical Society.

Dhinakar S. Kompala and Sadettin S. Ozturk, "Optimization of High Cell Density Perfusion Bioreactors," *Cell Culture Technology for Pharmaceutical and Cell-Based Therapies*, Ozturk, S. S. H., Wei-Shou, Ed. Taylor & Francis, pp. 387-416, New York, 2006.

G. Bernard-Michel, A. Monavon, D. Lhuillier, D. Abdo and H. Simon, "Particle velocity fluctuations and correlation lengths in dilute sedimenting suspensions," *Physics of Fluids*, vol. 14, No. 7, pp. 2339-2349, Jul. 2002, American Institute of Physics.

T. Nottorf, W. Hoera, H. Buentemeyer, S. Siwiora-Brenke, A. Loa, J. Lehmann, "Production of Human Growth Hormone in a Mammalian Cell High Density Perfusion Process," R. Smith (ed.), *Cell Technology for Cell Products*, pp. 789-793, 2007 Springer.

David R. Lloyd, Paul Holmes, Lee P. Jackson, A. Nicholas Emery and Mohamed Al-Rubeai, "Relationship between cell size, cell cycle and specific recombinant protein productivity," *Cytotechnology*, vol. 34, pp. 59-70, 2000 Kluwer Academic Publishers, printed in the Netherlands.

Manfred Hülscher, Uwe Scheibler, and Ulfert Onken, "Selective Recycle of Viable Animal Cells by Coupling of Airlift Reactor and Cell Settler," *Biotechnology and Bioengineering*, vol. 39, pp. 442-446, (1992); published by John Wiley & Sons, Inc.

Walter Puls and Herbert Kuhl, "Settling Velocity Determination Using the Bigdan Settling Tube and the Owen Settling Tube," *Journal of Sea Research* (*1996*), vol. 36 (1/2), pp. 119-125.

Jonathan S. Olshaker, M.D., and David A. Jerrard, M.D., "The Erythrocyte Sedimentation Rate," *The Journal of Emergency Medicine*, vol. 15, No. 6, pp. 869-874, 1997, Elsevier Science Inc., printed in the USA.

James A. Searles, Paul Todd, and Dhinakar S. Kompala, Viable Cell Recycle with an Inclined Settler in the Perfusion Culture of Suspended Recombinant Chinese Hamster Ovary Cells, *Biotechnol. Prog.* 1994, vol. 10, pp. 198-206, 1994 The American Chemical Society and American Institute of Chemical Engineers.

C. De Dobbeleer, M. Cloutier, M. Fouilland, R. Legros, and M. Jolicoeur, "A High-Rate Perfusion Bioreactor for Plant Cells," *Wiley InterScience*, pp. 1126-1137, published online Jun. 28, 2006 (www.interscience.wiley.com); 2006 Wiley Periodicals, Inc.

Zhi-You Wen, Xiao-Wei Teng, and Feng Chen, "A novel perfusion system for animal cell cultures by two step sequential sedimentation," *Journal of Biotechnology*, 2000, vol. 79, pp. 1-11, 2000 Elsevier Science B.V.

Yannick Peysson and Élisabeth Guazzelli, "An Experimental Investigation of the Intrinsic Convection in a Sedimenting Suspension," *Phys. Fluids*, vol. 10, No. 1, Jan. 1998, pp. 44-54, 1998 American Institute of Physics.

Amazile B. R. A. Maia and David Lee Nelson, "Application of Gravitational Sedimentation to Efficient Cellular Recycling in Continuous Alcoholic Fermentation," *Biotechnology and Bioengineering*, vol. 41, pp. 361-369 (1993), 1993 John Wiley & Sons, Inc.

M. Al-Rubeai, S. Chalder, R. Bird and A. N. Emery, Cell cycle, cell size and mitochondrial activity of hybridoma cells during batch cul-

(56) References Cited

OTHER PUBLICATIONS tivation, *Cytotechnology*, vol. 7, pp. 179-186, (1991) 1991 Kluwer Academic Publishers, printed in the Netherlands.

Thomas Seewöster and Jürgen Lehmann, "Cell Size Distributions as a Parameter for the Predetermination of Exponential Growth During Repeated Batch Cultivation of CHO Cells," *Biotechnology and Bioengineering*, vol. 55, No. 5, Sep. 5, 1997, pp. 793-797, 1997 John Wiley & Sons, Inc.

Irene Shackel, Amy Bass, Arno Brewer, Peter Brown, Mary C. Tsao and Lucille W. S. Chang, "Comparison of Manufacture Technologies for RAV12 Monoclonal Antibody in Production Medium Containing No Animal Derived Proteins," R. Smith (*ed.*), *Cell Technology for Cell Products*, pp. 761-763, 2007 Springer.

\* cited by examiner

METHOD AND SYSTEM FOR PARTICLE SETTLING VELOCITY MEASUREMENT

This application is a National Stage Entry of PCT/US2009/036031, claiming the benefit of and priority to U.S. Provisional Application No. 61/033,475, filed Mar. 4, 2008.

BACKGROUND OF THE INVENTION

The present invention is related to a method, a system, and a device for measuring particle settling velocity. In an exemplary embodiment, the invention is related to a method, a system, and a device for measuring the settling velocity of various particles in fields such as wastewater treatment, food processing, polymer and pigment technologies. The invention is particularly useful for measuring the settling velocity of biological entity such as cells in a suspension with a gravity settler e.g. a settling column, and can be widely applied in biotechnology and pharmaceutical fields, for example, to improve the efficiency of a perfusion cell culture process involving gravity settler for cell separation.

Accurate cell settling velocity determination is critical for perfusion culture using a gravity settler for cell retention. Gravity settlers have been successfully applied as cell retention devices in perfusion cell cultures from the bench-top to large-scale industrial applications, as disclosed in Batt, B.; Davis, R.; Kompala, D., Inclined sedimentation for selective retention of viable hybridomas in a continuous suspension bioreactor. Biotechnology Progress 1990, 6(6), 458-464; Choo, C. Y.; Tian, Y.; Kim, W. S.; Blatter, E.; Conary, J.; Brady, C. P., High-level production of a monoclonal antibody in murine myeloma cells by perfusion culture using a gravity settler. Biotechnol. Prog. 2007, 23(1), 225-231; Searles, J.; Todd, P.; Kompala, D., Viable cell recycle with an inclined settler in the perfusion culture of suspended recombinant chinese hamster ovary cells. Biotechnology Progress 1994, 10(2), 198-206; Wen, Z.-Y.; Teng, X.-W.; Chen, F., A novel perfusion system for animal cell cultures by two step sequential sedimentation. Journal of Biotechnology 2000, 79(1), 1-11; Shackel, I.; Bass, A.; Brewer, A.; Brown, P.; Tsao, M.; Chang, L., Comparison of manufacture technologies for rav12 monoclonal antibody in production medium containing no animal derived proteins. In Cell Technology for Cell Products, 2007; pp 761-763; Amazile B. R. A. Maia, D. L. N., Application of gravitational sedimentation to efficient cellular recycling in continuous alcoholic fermentation. Biotechnology and Bioengineering 1993, 41(3), 361-369; and Nottorf, T.; Hoera, W.; Buentemeyer, H.; Siwiora-Brenke, S.; Loa, A.; Lehmann, J., Production of human growth hormone in a mammalian cell high density perfusion process. In Cell Technology for Cell Products, 2007; pp 789-793.

The capacity of an inclined gravity settler to clarify cell suspension is described in equation (1):

$$S(v) = v \cdot s_p \quad (1)$$

where $S(v)$ is the volumetric flow rate of fluid clarified of particles with sedimentation velocity $v$; $s_p$ is the projection area of an inclined gravity settler, given by $w(L \sin\theta + b \cos\theta)$; $w$ is the settler width, $b$ is the separation between the two inclined surfaces, $L$ is the length of the settler, and $\theta$ is the angle of inclination of the settler from the vertical. Batt et al. and Davis et al. have successfully predicted the cell retention efficiency of gravity settlers based on theoretically calculated cell settling velocities in Batt, B.; Davis, R.; Kompala, D., Inclined sedimentation for selective retention of viable hybridomas in a continuous suspension bioreactor, Biotechnology Progress 1990, 6(6), 458-464; and in Davis, R. H.; Lee, C. Y.; Batt, B. C.; Kompala., D. S., Cell separations using differential sedimentation in inclined settlers, in Cell separation science and technology, Dhinakar S. Kompala, P. T., Ed. 1991; pp 113-127.

As disclosed in Batt, B.; Davis, R.; Kompala, D., Inclined sedimentation for selective retention of viable hybridomas in a continuous suspension bioreactor, Biotechnology Progress 1990, 6(6), 458-464; and Searles, J.; Todd, P.; Kompala, D., Viable cell recycle with an inclined settler in the perfusion culture of suspended recombinant chinese hamster ovary cells. Biotechnology Progress 1994, 10(2), 198-206, the accurate determination of the viable cell sedimentation velocity is critical for controlling the operation of the gravity settler to minimize viable cell loss and maximize nonviable cell removal, and thus maximize viable cell concentration in the bioreactor. During long-term perfusion culture, the cell suspension is a mixture of viable and nonviable cells, and the nonviable cells have settling velocities that are less than that of the viable cells. Viable cell settling velocity can vary significantly among mammalian cell lines; for instance, the settling velocity of hybridoma cell line AB2-143.2 and CHO cell line M1-59 are 2.9 cm/hr and 1.45 cm/hr respectively, as disclosed in Searles, J.; Todd, P.; Kompala, D., Viable cell recycle with an inclined settler in the perfusion culture of suspended recombinant Chinese hamster ovary cells. Biotechnology Progress 1994, 10(2), 198-206. This two-fold difference demonstrates the necessity of measuring this parameter for every new cell line to be used in a gravity settler/perfusion system in order to properly select the gravity settler with appropriate capacity.

It is important to measure the distinct settling velocity of the viable and nonviable cell populations periodically during a long-term perfusion culture in order to optimize the operation of the gravity settler in real-time, because the settling velocity of viable cells may change substantially during the course of a long-term perfusion culture due to changes in cell size, as disclosed in Frame, K. K.; Hu, W.-S. Cell volume measurement as an estimation of mammalian cell biomass. Biotechnol. Bioeng. 1990, 36, 191-197; Martens D. E.; de Gooijer C. D.; van der Velden-de Groot C. A. M.; Beuvery E. C.; Tramper J. Effect of dilution rate on growth, productivity, cell cycle and size, and shear sensitivity of a hybridoma cell in a continuous culture. Biotechnol. Bioeng. 1993, 41, 429-439.

The measurement of erythrocyte sedimentation rate (ESR) has been widely used for over 50 years as a simple, standardized medical screening test, which has been disclosed in for example Council for Standardization in Haematology (Expert Panel on Blood Rheology), ICSH recommendations for measurement of erythrocyte sedimentation rate. J Clin Pathol. 1993, 46(3), 198-203; Woodland, N. B.; Cordatos, K.; Hung, W. T.; Reuben, A.; Holley, L., Erythrocyte sedimentation in columns and the significance of ESR. Biorheology 1996, 33(6), 477-488; Rabjohn, L.; Roberts, K.; Troiano, M.; Schoenhaus, H., Diagnostic and prognostic value of erythrocyte sedimentation rate in contiguous osteomyelitis of the foot and ankle. The journal of Foot and Ankle Surgery 2007, 46(4), 230-237; Mönig, H.; Marquardt, D.; Arendt, T.; Kloehn, S. Limited value of elevated erythrocyte sedimentation rate as an indicator of malignancy. Fam. Pract. 2002, 19, 436-438; Olshaker, J. S.; Jerrard, D. A., The erythrocyte sedimentation rate. Journal of Emergency Medicine 1997, 15(6), 869-874; and Erikssen, G.; Liestol, K.; Bjonholt, H.; Stormorken, H.; Thaulow, E.; Erikssen, J., Erythrocyte sedimentation rate: a possible marker of atherosclerosis and a strong predictor of coronary heart disease mortality. European Heart Journal 2000, 21(19), 1614-1620.

Many modifications have been made to speed-up the procedure, for example, Drucker, K. G. Sedimentation rate centrifuge and method determining sedimentation rate. U.S. Pat. No. 3,199,775, 1965; Winkelman, J. W.; Tanasijevic, M. J.; Bennett, M. Method and apparatus for determining erythrocyte sedimentation rate and hematocrit. U.S. Pat. No. 6,506,606, 2003; Bull, B. S. Method and apparatus for rapid determination of blood sedimentation rate. U.S. Pat. No. 5,594,164, 1997. However, the basic operational principle remains the same. A sample of blood is placed in a narrow tube (Westergren Tube) and after a period of time a visible interface forms between the clarified plasma and the red blood cells. By reading the scale at the interface after a defined period of time the sedimentation can be determined. This method assumes the red blood cells have uniform size and settling velocity; therefore the movement of the red blood cell population is taken as the distance that the cells at the top of the tube can move in certain time. This method is not directly applicable to mammalian cell culture, since there is not a clear color difference between the cells and the clarified supernatant. For the same reason, the method used to determine plant cell settling velocity is not practical for animal cell culture, as explained in De Dobbeleer, C.; Cloutier, M.; Fouilland, M.; Legros, R.; Jolicoeur, M., A high-rate perfusion bioreactor for plant cells. *Biotechnology and Bioengineering* 2006, 95(6), 1126-1137. Even if there is a clearly identifiable interface, only the settling velocity of the smallest nonviable cells can be determined in this manner. This measurement is much less important than that of the viable cells for optimizing the gravity settler operation.

Particle image velocimetry (PIV) has been used primarily for determining the settling velocity of individual particles in Guazzelli, É., Evolution of particle-velocity correlations in sedimentation, *Physics of Fluids* 2001, 13(6), 1537-1540. Despite the complexity of this process, it cannot distinguish between viable and nonviable cell settling velocity.

Another method, the "Owen Tube", is a 1-L column used for determining the settling velocity of suspended particulate matter in natural body water, as disclosed in Dearnaley, M. P., Direct measurements of settling velocities in the owen tube: A comparison with gravimetric analysis. *Journal of Sea Research* 1996, 36(1-2), 41-47; Wolfstein, K., Fractionation and measurements of settling velocities of suspended matter using an owen tube. *Journal of Sea Research* 1996, 36(1-2), 147-152; and Puls, W.; Kühl, H., Settling velocity determination using the BIGDAN settling tube and the Owen settling tube. *Journal of Sea Research* 1996, 36(1-2), 119-125. Periodic samples are removed from the bottom of the Owen Tube and the dry weight measurement is used to determine the settling velocity. However, this method is not accurate for small sample amounts, the presence of cell debris would contribute to measurement error, and the process cannot distinguish the viability of the cells.

Stokes' law can be used to estimate the settling velocity of particles in fluid when the Reynold's number is less than 0.2, given by:

$$v = \frac{g d_p^2 (\rho_p - \rho)}{18\mu} \quad (2)$$

where $d_p$=particle diameter; $\mu$=fluid viscosity; $\rho_p$=density of solid particle; $\rho$=density of carrying fluid; g is acceleration due to gravity. The particle diameter is normally determined by means of a Particle Size Analyzer (Particle Data Inc.) or Coulter Multisizer (Beckman Coulter, Fullerton, Calif.). The particle density is measured using neutral buoyancy measurement or density gradient partitioning methods. A glass capillary viscometer can be used to determine the fluid viscosity. The fluid density is easily determined from weight and volume measurements. Using this procedure, the settling velocity of viable and nonviable hybridoma and CHO cells have been determined in Batt, B.; Davis, R.; Kompala, D., Inclined sedimentation for selective retention of viable hybridomas in a continuous suspension bioreactor. *Biotechnology Progress* 1990, 6(6), 458-464; and Searles, J.; Todd, P.; Kompala, D., Viable cell recycle with an inclined settler in the perfusion culture of suspended recombinant chinese hamster ovary cells. *Biotechnology Progress* 1994, 10(2), 198-206. However, this method is not practical for routine measurements during long-term perfusion culture since multiple measurements are needed for a single settling velocity determination, which is time-consuming and increases the potential for measurement error.

Advantageously, the present invention provides a simple, inexpensive, accurate, and rapid method for measuring settling velocity of particles such as polystyrene, and viable and nonviable cells in a mixed population, among others.

BRIEF DESCRIPTION OF THE INVENTION

One aspect of the invention provides a method of measuring particle settling velocity comprising:
(i) providing a gravity settler such as a column;
(ii) filling the column with a first homogenous particle suspension, wherein the particle concentration in the first homogenous particle suspension is $X_1$;
(iii) separating the column into an upper sub-column and a lower sub-column with a height h after settling the first homogenous particle suspension for a period of time t, wherein some particles remain in the upper sub-column;
(iv) removing the particle suspension in the upper sub-column and mixing the particle suspension confined in the lower sub-column with a height h to prepare a second homogenous particle suspension;
(v) measuring the particle concentration in the second homogenous particle suspension $X_2$; and
(vi) determining the particle settling velocity v with the formula: $v=h(X_2-X_1)/tX_1$.

Another aspect of the invention provides a system for measuring particle settling velocity comprising:
(i) a gravity settler such as a column;
(ii) a separator;
(iii) a means for measuring the particle concentration in a particle suspension;
(iv) a timer; and
(v) a leveled surface for holding the column upright;
wherein the separator can vertically separate the column into an upper sub-column and a lower sub-column.

Still another aspect of the invention provides an automatic system for measuring particle settling velocity comprising:
(i) a gravity settler such as a column;
(ii) a separator;
(iii) a means for measuring the particle concentration in a particle suspension;
(iv) a timer; and
(v) a leveled surface for holding the column upright;
wherein the separator can vertically separate the column into an upper sub-column and a lower sub-column.

A further aspect of the invention provides a device for measuring particle settling velocity comprising:
(i) a gravity settler such as a column;
(ii) a separator; and
(iii) a leveled surface for holding the column upright;

wherein the separator can separate the column vertically into an upper sub-column and a lower sub-column.

DETAILED DESCRIPTION OF THE INVENTION

Figure 1A:
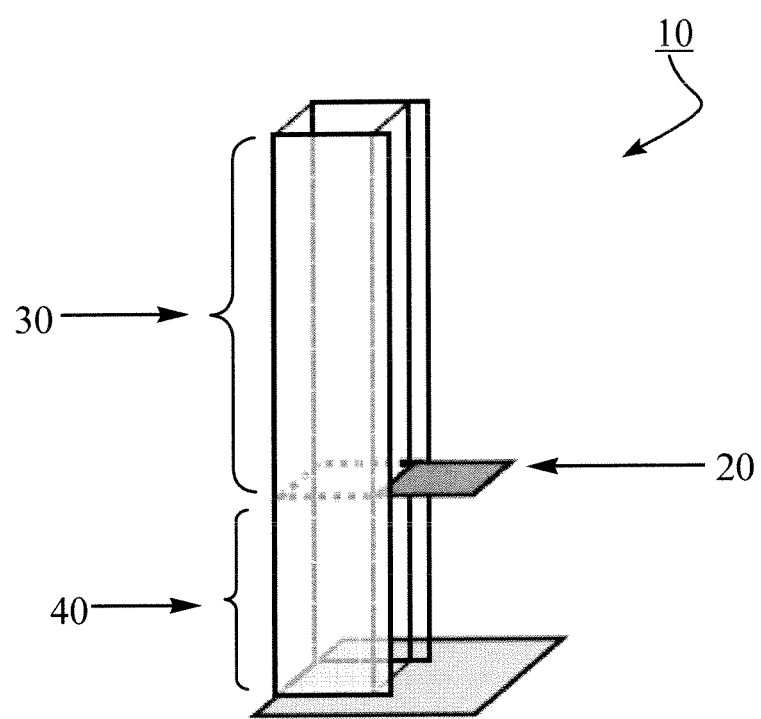
FIG. 1A shows an exemplary device for measuring particle settling velocity according to an embodiment of the present invention.

In an embodiment, a device for measuring particle settling velocity is made based on a modification of the Westergren Tube. With reference to FIG. 1A, an exemplary device for measuring particle settling velocity comprises a gravity settler such as a settling column 10; and a separator such as a shutter 20. Separator 20 can be opened and closed, and when it is closed, it separates column 10 vertically into an upper sub-column 30 and a lower sub-column 40.

Figure 1B:
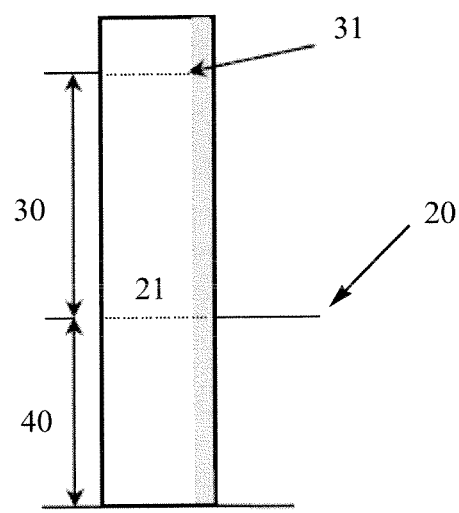
FIG. 1B shows the side view of an exemplary device for measuring particle settling velocity according to an embodiment of the present invention.

A specific exemplary device may be constructed with a side view as illustrated in FIG. 1B. With reference to FIGS. 1A and 1B, the device 10 is constructed of 2.4 mm glass plate, with 11.5 cm height, 1.4 cm internal width and 2 cm internal length or depth. There is a 0.6 mm wide slot in the narrow side of the column, at a distance of 4 cm from the bottom. At the same height as the slot is a 0.6 mm wide and 0.5 mm deep groove 21 on the other three sides of the glass walls. Groove 21 is filled with silicone glue (General Electric). The edge of the plate glass at the slot is also coated with the silicone glue. A shutter 20 is made of 0.5 mm thick and 4.5 cm long stainless steel plate which is slightly wider than the width of the slot. Groove 21 in the glass works as a track to guide the shutter through the slot. The function of the silicone glue is to help seal the contact between the shutter and glass surface. When conducting the settling velocity measurement, high vacuum grease was also applied to the interface between the glass plate and shutter 20 to help seal the contacts. When shutter 20 is pushed into the column, lower sub-column 40 can be totally closed.

A leveled surface may be used for holding the column 10 upright. For example, such leveled surface may be a plate attached with a leveling device. In FIGS. 1A and 1B, settling column 10 is exactly perpendicular to the supporting 7 cm×7 cm glass plate, to which it is glued. The device is preferably located on a leveled horizontal surface so settling column 10 is strictly vertical. In measurement, the particle suspension may be filled to suspension (liquid) fill position 31, which is at a distance of, for example, 6 cm from the position of shutter 20.

The invention further provides a system for measuring particle settling velocity comprising:
(i) a gravity settler such as the settling column as shown in FIGS. 1A and 1B;
(ii) a separator such as the shutter as shown in FIGS. 1A and 1B;
(iii) a means for measuring the particle concentration in a particle suspension; and
(iv) a timer;
wherein the separator can vertically separate the column into an upper sub-column and a lower sub-column.

Such a system may be automated by, for example, including a computational hardware, such as for example, a microprocessor, computer processor, digital signal processor, or micro-controller.

In a preferred embodiment, the device and system of the invention may use a gravity settler with real-time adjustable capacity (such as length and volume).

Figure 2:
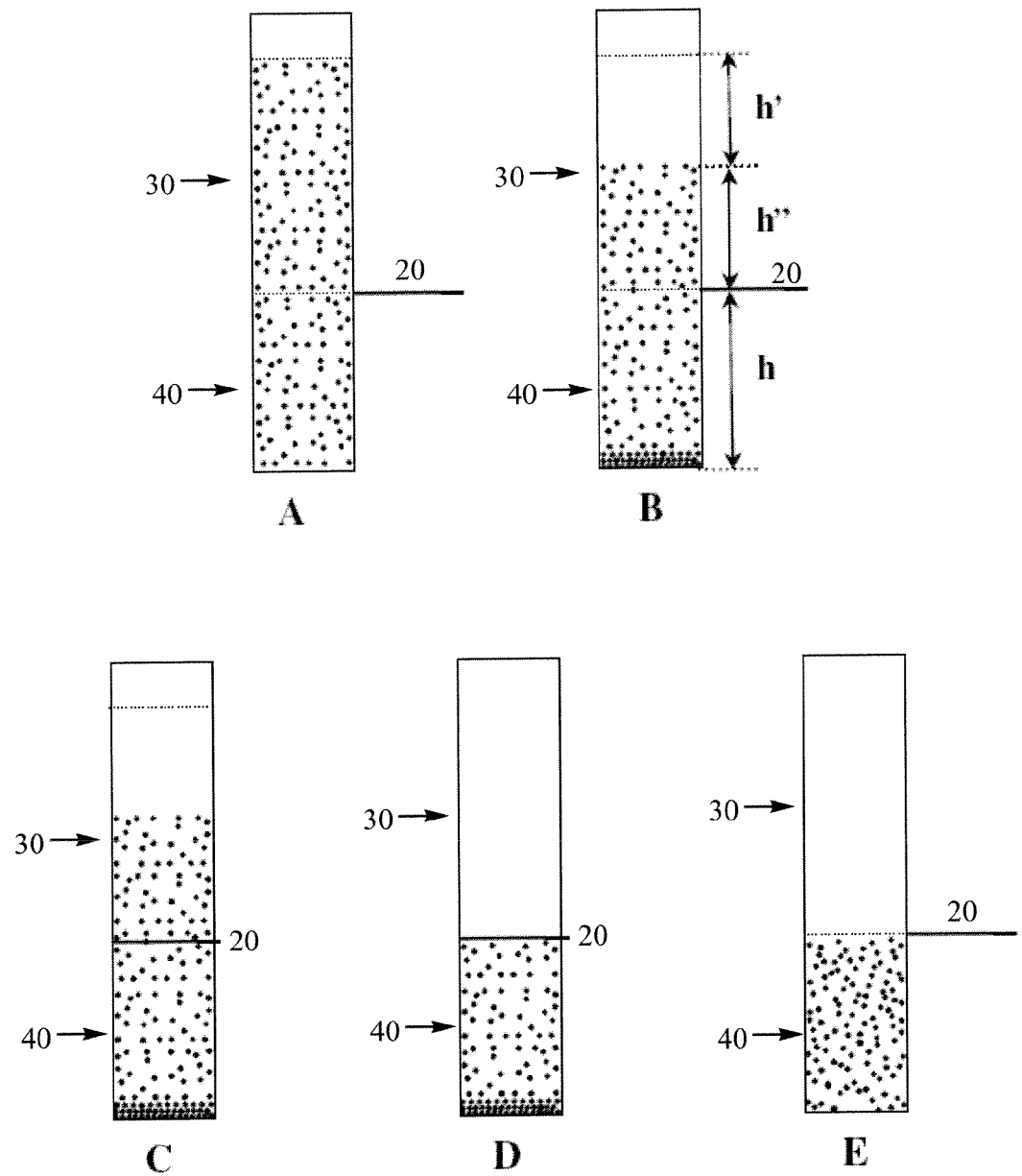
FIGS. 2A-2E illustrate the method of measuring particle settling velocity according to an embodiment of the present invention.

With reference to FIGS. 2A-2E, a method of measuring particle settling velocity is illustrated. In FIGS. 2A-2E, the column can be separated by a separator such as a shutter 20 into an upper sub-column 30 and a lower sub-column 40 with a height h. In FIG. 2A, the column (shutter 20 is open) is filled with a first homogenous particle suspension such as well mixed monodisperse particle suspension with known particle concentration $X_1$. Any known methods can be used to measure the particle concentration in the invention. For example, a Coulter Counter may be used for determining polystyrene particle number. Cells can be counted visually in a hemocytometer with a light microscope. In an embodiment, the method of trypan blue exclusion is used to determine the concentration of the viable (clear cells) and the nonviable cells (stained blue).

In FIG. 2B, shutter 20 remains open, and the particles in the column moved downwardly for example h' distance in a period of time t such as one hour. In FIG. 2C, shutter 20 is closed by pushing and it separates the column in two parts, i.e. upper sub-column 30 and lower sub-column 40, to stop particles from moving into lower sub-column 40 while some particles remain in upper sub-column 30 (the h" region). In FIG. 2D, the particle suspension above the shutter 20 (in upper sub-column 30) is removed. In FIG. 2E, the particle suspension confined in lower sub-column 40 with a height h is mixed to prepare a second homogenous particle suspension. For example, the settled particles from the bottom of the column are re-suspended and well mixed. Then the second homogenous particle suspension from lower sub-column 40 is sampled and measured to determine the particle concentration $X_2$. Finally, the particle settling velocity v may be calculated with the formula:

$$v = h(X_2 - X_1)/tX_1$$

The device of the invention may be designed to measure particle settling velocity v ranging broadly from about 0.1 cm/hr to about 100 cm/hr, preferably from about 0.5 cm/hr to about 60 cm/hr, and more preferably from about 1 cm/hr to about 10 cm/hr. For example, mammalian cells typically have settling velocities less than 6 cm/hr. The settling velocity of bigger particles, which settle much faster than the cells such as hybridoma cell lines, e.g. HB-159 (ATCC), 9E10 (ATCC) and R73, can be measured simply by increasing the height of the column without increasing the distance between the shutter and bottom, that is, h.

The invention can be used to measure the settling velocity of any particles, such as spherical, regularly- or irregularly-shaped particles or cells. In exemplary embodiments of the invention, the settling velocity of polystyrene particles was measured to test the method and device of the invention. For example, monodisperse standard polystyrene particles (Sigma, St. Louis, Mo.) with 15 um diameter and 1.05 g/mL density were used to verify the reliability of the device. The particles were suspended in de-ionized (DI) water supplemented with 0.1% Triton X-100 (Sigma, St. Louis, Mo.), which helps prevent the particles from coagulating. The viscosity of the solution (without the particles) at 28° C. is 0.0084 poise, as measured using a size 25 glass capillary viscometer (Cannon Instrument Co. State College, Pa.). The density of the fluid is 996 kg/m$^3$. The concentration of the particle suspension is $1.8 \times 10^5$ particles/mL, resulting in 0.03% volume fraction. All the particle settling velocity measurements were conducted in a 28° C. incubator. The polystyrene particles were counted using a Z2 Coulter Counter (Beckman Coulter, Fullerton, Calif.) equipped with a 70 um ampoule aperture tube. The lower threshold was set at 14 um and higher threshold was 16 um.

A sample containing 28 mL of the well-mixed monodisperse particle suspension was added to the settling column (FIG. 2A) with the shutter open. Assuming uniform particle density and diameter, the particles settle down at the same rate, traveling a distance h' over the settling time period t (FIG. 2B). The particle settling velocity is given by:

$$v = \frac{h'}{t} \quad (3)$$

The volume of the column vacated by the particles is given by:

$$V' = h' \cdot s \quad (4)$$

where s is the cross section area of the settling column. Similarly, the volume below the shutter, V, and the volume between the shutter and the interface, V'', are given by:

$$V = h \cdot s \quad 5(a)$$

$$V'' = h'' \cdot s \quad 5(b)$$

At time=t, the shutter is closed (FIG. 2C), and the particle suspension above the shutter is removed (FIG. 2D). The settled particles on the bottom of the column are then resuspended and thoroughly mixed with the remaining particle suspension below the shutter. Mass is conserved between time=0 and time=t, yielding:

$$X_1(V' + V'' + V) = X_1 V'' + X_2 V \quad (6)$$

where $X_1$ is the particle concentration in the initial suspension added to the column; V is the volume of the column below the shutter; and $X_2$ is the particle concentration after re-suspending and mixing the settled particles in the space below the shutter (FIG. 2E).

Rearranging Equation 6 yields:

$$V' = \frac{V(X_2 - X_1)}{X_1} \quad (7)$$

Combining Equations 3 and 4 yields:

$$v = \frac{V'}{st} \quad (8)$$

and substituting Equations 7 and 5a into Equation 8 yields:

$$v = \frac{h(X_2 - X_1)}{t X_1} \quad (9)$$

The distance h is fixed by the device design and $X_1$ is known from the sample preparation. The experiment is conducted for a known amount of time t, such that the particle interface remains above the shutter position during the time t. Therefore the only measurement needed is that of the particle concentration in the lower volume.

The settling velocity of 15 um polystyrene particles at 28° C. was calculated using Equation 1 to be 2.81 cm/hour. To confirm the applicability of Stokes' law to this system, the Reynolds number was calculated using:

$$Re = \rho_p d_p v / \mu \quad (10)$$

The calculated Re number is 0.0014, indicating that the settling velocity is indeed governed by Stokes' law.

According to Sakiadis, B. C., Fluid and Particle Mechanics. In *Perry's Chemical Engineers' Handbook*, 6th ed.; Perry, R. H.; Green, D. W.; Maloney, J. O., Eds. McGraw-Hill: New York, 1984; pp 5-63~5-68, the corrected settling velocity can be calculated taking into account particle concentration and wall effects by means of:

$$v_{ts} = v(1-c)^n / (1+2.1\beta) \quad (11)$$

where $v_{ts}$ is the corrected settling velocity, v is the settling velocity of a single particle calculated from Stokes' law; c is the volume fraction of the particles in the fluid; n is a function of Reynolds number, equal to 4.65 when Reynolds number is less than 0.3; and β is the ratio of particle diameter to vessel diameter. The hydraulic diameter is commonly used to calculate the equivalent diameter when handling flow in noncircular channels, defined as:

$$d_h = \frac{4A}{U} \quad (12)$$

where A is the area of the cross-section of the rectangular channel and U is the wetted perimeter of the cross-section. The hydraulic diameter of the settling column used here is 1.47 cm.

The corrected theoretical settling velocity for the polystyrene particles, calculated using Equation (11) with concentration of $1.8 \times 10^5$ particles/mL (volume fraction of 0.03%), is 2.80 cm/hour. The difference between the calculated value using Stokes' law and the corrected one is less than 0.4%, indicating that the effects of concentration and the wall are negligible.

Figure 3A:
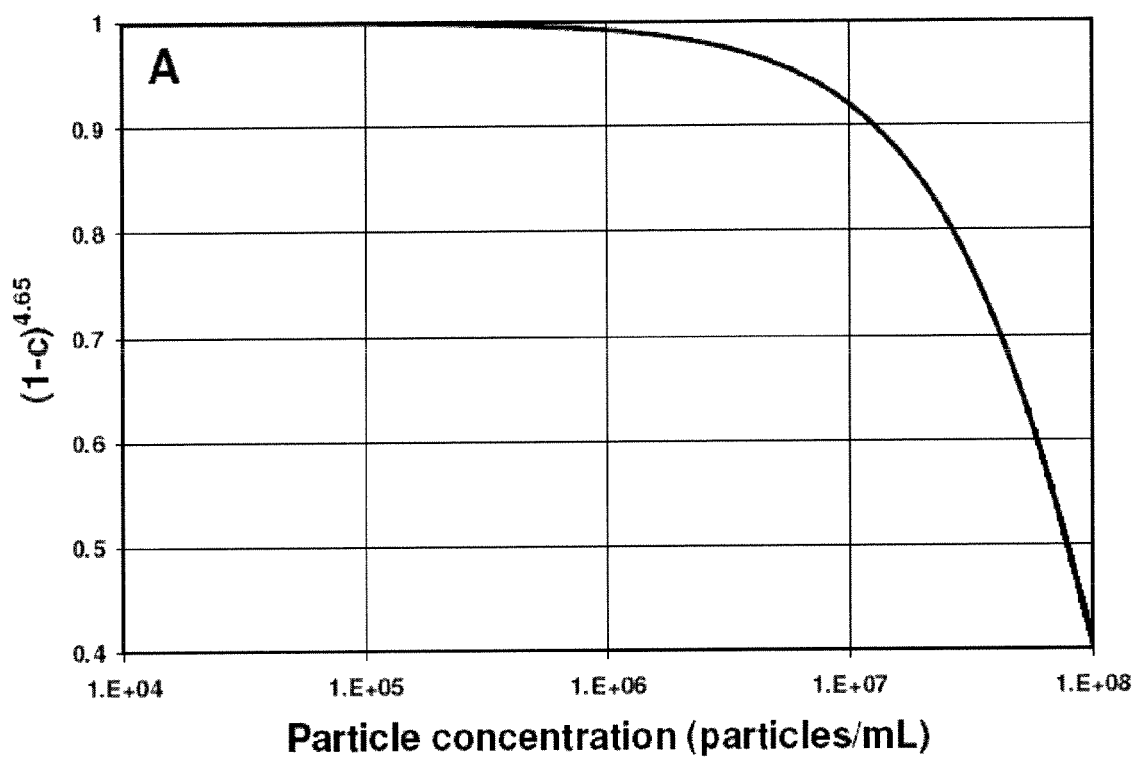
FIG. 3A demonstrates the concentration effect based on polystyrene particles with 15 um diameter according to an embodiment of the present invention.

FIG. 3A demonstrates the concentration effect based on polystyrene particles with 15 um diameter. As shown in FIG. 3A, at concentrations greater than $1 \times 10^6$ particles/mL, the concentration effect on settling velocity starts to increase noticeably; at concentrations greater than $1 \times 10^7$ particles/mL, the concentration effect on settling velocity increases sharply. Without compensation for the concentration effect, at cell concentrations of $5 \times 10^7$ cells/mL (expected during perfusion culture), the settling velocity calculated using Stokes' law has over 30% deviation from the actual settling velocity. The large effect of cell concentration on settling velocity demonstrates the advantage of a direct measurement of this property using the settling column, rather than a theoretical calculation using Stokes' law.

Figure 3B:
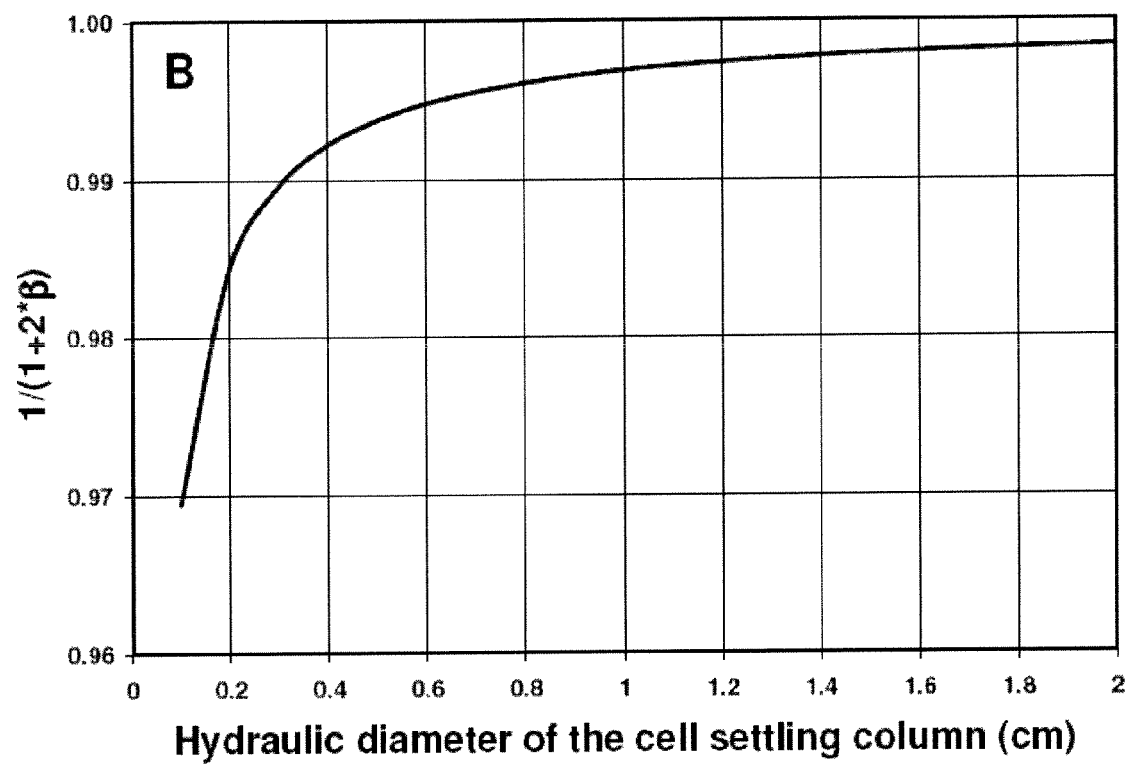
FIG. 3B demonstrates the wall effect based on polystyrene particles with 15 um diameter according to an embodiment of the present invention.

FIG. 3B demonstrates the wall effect based on polystyrene particles with 15 um diameter. As shown in FIG. 3B, the wall effect is still negligible even at half the hydraulic diameter of the current settling column prototype. This result indicates that the minimum cell suspension volume needed for use in the settling column can be reduced to less than 10 mL with no material impact on the accuracy of the measurement.

Figure 4:
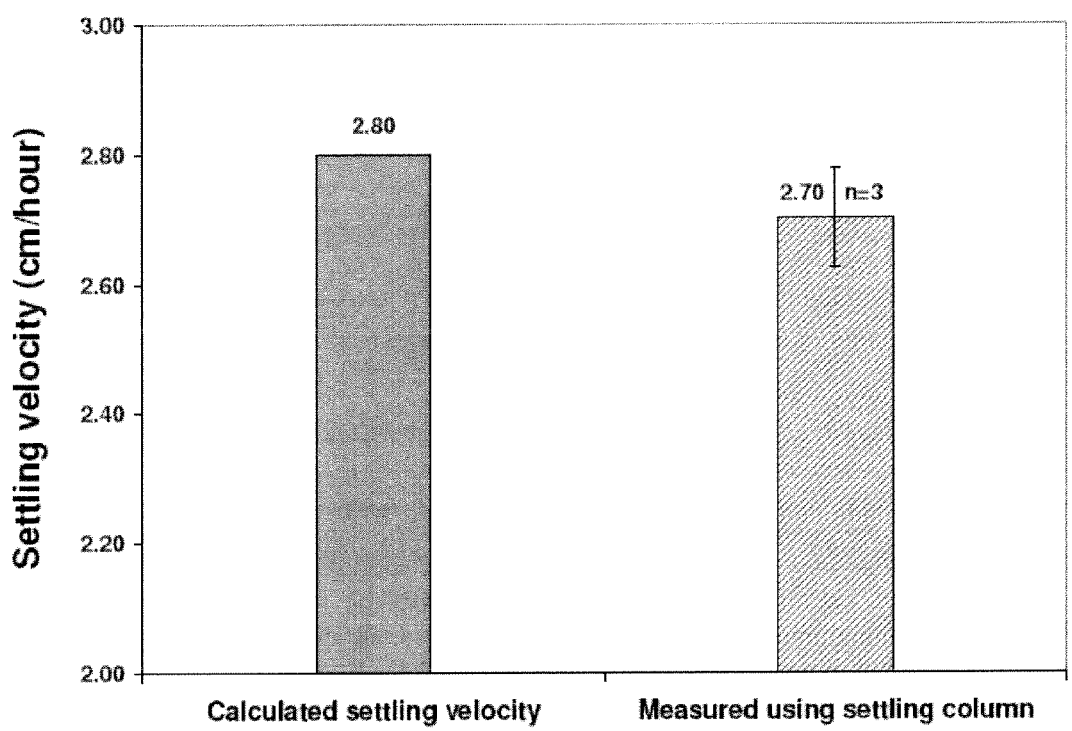
FIG. 4 shows the comparison of the settling velocities of 15 um polystyrene particles calculated using Stokes' law vs. that measured using a settling column according to an embodiment of the present invention.

FIG. 4 shows the comparison of the settling velocities of 15 um polystyrene particles, calculated using Stokes' law and the measurements with Equations (3)-(9) as described above (left) and measured using the settling column (right). The settling velocity of the polystyrene particles, measured using the settling column, is 2.70±0.08 cm/hour as shown in FIG. 4. This value is 3.6% smaller than the theoretical value, corrected for wall and concentration effects. This small deviation is most likely caused by particle inertial effects, which are difficult to predict according to Bernard-Michel, G.; Monavon, A.; Lhuillier, D.; Abdo, D.; Simon, H. Particle velocity fluctuations and correlation lengths in dilute sedimenting suspensions. *Phys. Fluids.* 2002, 14, 2339-2349; Peysson, Y.; Guazzelli, É. An experimental investigation of the intrinsic convection in a sedimenting suspension. *Phys. Fluids.* 1998, 10, 44-54; Segrè, P. N.; Herbolzheimer, E.; Chaikin, P. M. Long-range correlations in sedimentation. *Phys. Rev. Lett.* 1997, 79, 2574-2577; Sutterby, J. L. Falling sphere viscometry. I. Wall and inertial corrections to Stokes' law in long tubes. *J. Rheol.* 1973, 17, 559-573; Tee, S.-Y.; Mucha, P. J.; Cipelletti, L.; Manley, S.; Brenner, M. P.; Segre, P. N.; Weitz, D. A. Nonuniversal velocity fluctuations of sedimenting particles. *Phys. Rev. Lett.* 2002, 89, 054501~1-054501~4. It is almost impossible to totally avoid swirling or convective motion of the particle suspension. Particle inertia influences the settling velocity at both the micro-scale and macro-scale. In order to minimize the inertial effect by avoiding convection caused by a temperature difference, the settling column and particle suspension should be at the same temperature before the suspension is added to the column. Convection can also be reduced by the slow addition of the suspension to the column.

In exemplary embodiments of the invention, the settling velocities of biological particles such as viable and nonviable cells from various cell lines and cell cultures were also measured similarly to test the method and device of the invention, optionally using the polystyrene particles as standard particles. For example, three hybridoma cell lines, HB-159 (ATCC), 9E10 (ATCC) and R73 (Cleveland Clinic Foundation, Cleveland, Ohio), were tested with the settling column. All cells were cultured with BD Cell™ Mab serum free medium (BD Diagnostic Systems, Sparks, Md.) and maintained in 250 mL T-flasks in a 37° C. incubator with 5% carbon dioxide. Cell settling velocity measurements were conducted with cells in the exponential growth phase, in the second day after inoculation; and with cells in death phase, in the fifth day after inoculation. All cell settling velocity measurements were conducted in the 37° C. incubator. Cell size distribution measurements of HB-159 were conducted with cells cultured 2, 6, 9, 13 and 17 days after inoculation. The Z2 Coulter Counter was also used to determine the cell size distribution of the HB-159 cells. The cell concentration and viability were measured using a hemacytometer and trypan blue exclusion method. More than 1000 viable cells were counted for each sample.

Figure 5:
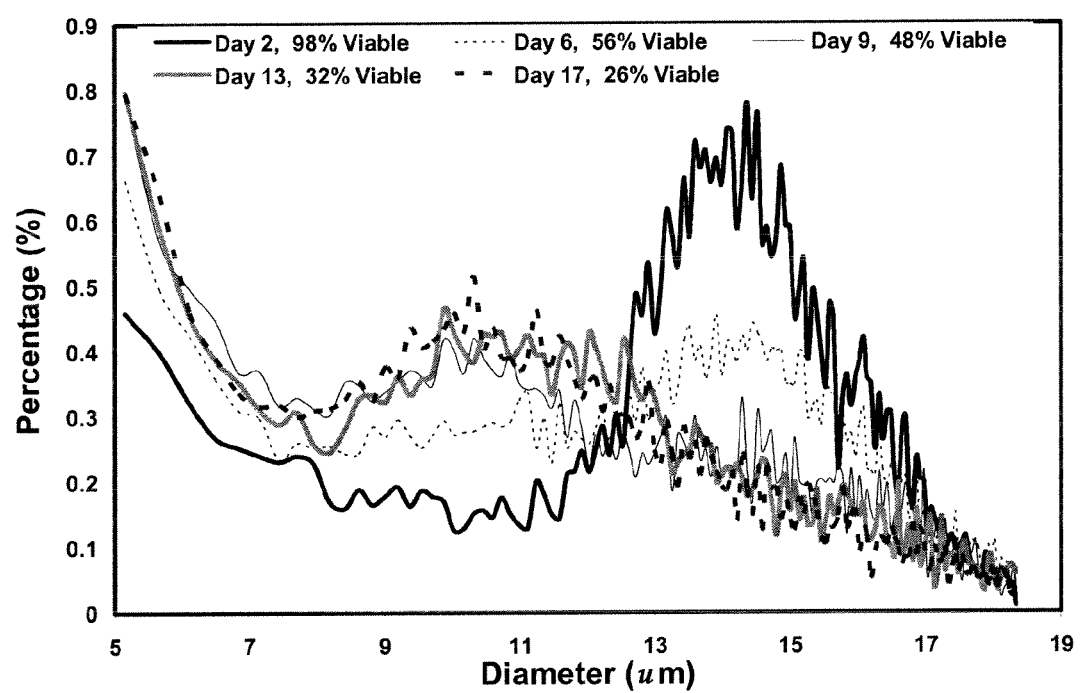
FIG. 5 shows the size distribution histogram of HB-159 Hybridoma cell cultured in 250 ml T-flask.

FIG. 5 shows the size distribution histogram of HB-159 Hybridoma cell cultured in 250 ml T-flask. The size distributions of the HB-159 hybridoma cell line at different lengths of time in culture are shown in FIG. 5. Two peaks are evident, at diameters of 10 μm and 14.5 μm. The percentage of cells with the lower diameter increased with decreasing viability while the percentage of cells at the higher diameter decreased with decreasing viability. The first peak at 10 μm most likely denotes nonviable cell population and the second peak at 14.5 μm denotes the viable cell population. These results are in agreement with results reported by Searles et at. (Searles, J.; Todd, P.; Kompala, D., Viable cell recycle with an inclined settler in the perfusion culture of suspended recombinant chinese hamster ovary cells. *Biotechnology Progress* 1994, 10(2), 198-206) in which the mean size of nonviable cells is significantly smaller than that of the viable cells. Not only are nonviable cells smaller than viable cells, but also the nonviable cells decrease in diameter as the population viability decreases according to Searles et al. It has also been reported that viable cell diameter increases over 20% when the cells progress from lag phase to exponential phase in Seewöster, T.; Lehmann, J., Cell size distribution as a parameter for the predetermination of exponential growth during repeated batch cultivation of CHO cells. *Biotechnology and Bioengineering* 1997, 55(5), 793-797; and Lloyd, D. R.; Holmes, P.; Jackson, L. P.; Emery, A. N.; Al-Rubeai, M., Relationship between cell size, cell cycle and specific recombinant protein productivity. *Cytotechnology* 2000, 34(1/2), 59-70.

Table 1 tabulates the settling velocities of the HB-159, R73 and 9E10 cell lines achieved using the settling column. The results for the hybridoma AB2-143.2 and CHO M1-59 cell lines were reported in other literatures.

TABLE 1

| Cell Line | Viability (%) | Settling Velocity (cm/h) | |
|---|---|---|---|
| | | Viable | Nonviable |
| Hybridoma HR-159 | 94 | 3.5 | N/A |
| | 64 | 2.8 | 1.7 |
| Hybridoma R73 | 96 | 1.8 | N/A |
| | 65 | 0.9 | 0.6 |
| Hybridoma 9E10 | 97 | 2.6 | N/A |
| | 65 | 1.8 | 0.9 |
| Hybridoma AB2-143.2 (Batt et al. 1990) (1) | N/A | 2.9 | 1.1 |
| CHO M1-59 (Searles et al. 1994) (4) | N/A | 1.4 | 0.86 |

Table 1 shows the settling velocities of three hybridoma cell lines measured using the settling column along with settling velocities of two cell lines reported in Batt, B.; Davis, R.; Kompala, D., Inclined sedimentation for selective retention of viable hybridomas in a continuous suspension bioreactor. *Biotechnology Progress* 1990, 6(6), 458-464; and Searles, J.; Todd, P.; Kompala, D., Viable cell recycle with an inclined settler in the perfusion culture of suspended recombinant chinese hamster ovary cells. *Biotechnology Progress* 1994, 10(2), 198-206. The variation in settling velocities of the three hybridoma cell lines is significant, with a two-fold variation between the HB-159 and the R73. These measurements are similar to values reported for a hybridoma cell line and a CHO cell line, obtained using Stokes' law, as disclosed in Batt, B.; Davis, R.; Kompala, D., Inclined sedimentation for selective retention of viable hybridomas in a continuous suspension bioreactor. *Biotechnology Progress* 1990, 6(6), 458-464; and Searles, J.; Todd, P.; Kompala, D., Viable cell recycle with an inclined settler in the perfusion culture of suspended recombinant chinese hamster ovary cells. *Biotechnology Progress* 1994, 10(2), 198-206. The two-fold variation in settling velocities indicates that the cell line with the lower velocity will need a gravity settler that is double in size to achieve the same cell retention capacity as that of the faster-settling cell line. This confirms the necessity of measuring the settling velocity before selecting the gravity settler and starting the perfusion culture.

In Table 1, the settling velocities of the nonviable cells are 30-50% lower than the corresponding viable settling velocity. The nonviable cell settling velocity was measured only when the population viability was lower than 70% in order to obtain enough nonviable cells to be counted accurately using a hemacytometer. This difference is the basis of preferential removal of nonviable cells using gravity settler in perfusion culture bioreactors.

Table 1 also shows that even for the same cell line, the viable cell settling velocity decreases significantly, up to 50%, when viability of the cell suspension decreases from 97% to 65%. Since a lowered viability is a normal outcome during long-term perfusion culture, this result indicates that the minimum capacity of the gravity settler would need to be doubled to maintain the cell retention efficiency throughout the culture period. Otherwise, loss of viable cells would likely occur, especially when the cell viability drops significantly according to Thompson, K., Wilson, J. Particle settler for use in cell culture, U.S. Pat. No. 5,817,505 1998. Therefore it is necessary to measure the cell settling velocity periodically during the perfusion culture.

The present invention provides numerous advantages and benefits. For example, the settling column of the invention provides an inexpensive, rapid, and accurate method for determining settling velocities of particles such as cells. The method of the invention was established using polystyrene particles with known physical properties, and resulted in less than 4% error compared to the theoretical value obtained using Stokes' law. The method can be used to measure the settling velocity of cells such as three different hybridoma cell lines. The settling velocities of three hybridoma cell lines were measured, resulting in up to two-fold variation among cell lines, and the values decreased as the cell culture aged. The settling velocities of the nonviable cells were 33-50% less than the corresponding viable cells. Therefore, the method of the invention can distinguish the settling velocities of viable and nonviable cells, which is important for maximizing viable cell retention and nonviable removal in perfusion systems. The significant variation of settling velocities among cell populations and growth phases confirms the necessity of routine measurement of this property during long-term perfusion culture.

The settling velocity differs significantly among cell lines and it changes substantially when cell viability drops for same cell line. The cell settling velocity measurement should thus be performed routinely for each cell line both before and during the perfusion culture when a gravity settler is used for cell retention. In this way a gravity settler with enough capacity can be selected a priori to maximize viable cell retention and nonviable removal efficiency. Furthermore, the time-dependency of the cell size and thus the settling velocity indicates that a gravity settler with real-time adjustable capacity is preferred for optimal cell retention.

In an embodiment, the method transfers the cell settling velocity measurement into a cell counting procedure, which is simpler to obtain than the multiple measurements needed for a Stokes' law calculation. This method can be further simplified by use of automated cell counting equipment that can distinguish between viable and nonviable cells rather than the traditional hemacytometer.

Furthermore, Stokes' law assumes that the cells are perfectly spherical, while the settling column can be used to measure the true settling velocity of irregularly-shaped particles or cells.

Several embodiments have been described with reference to the preferred embodiments. Obviously, modifications and alterations will occur to others upon reading and understanding the preceding detailed description. It is intended that the exemplary embodiment be construed as including all such modifications and alterations insofar as they come within the scope of the appended claims or the equivalents thereof.

The invention claimed is:

1. A method of measuring particle settling velocity comprising:
    (i) providing a gravity settler;
    (ii) filling the column with a first homogenous particle suspension, wherein the particle concentration in the first homogenous particle suspension is $X_1$;
    (iii) separating the column into an upper sub-column and a lower sub-column with a height h after settling the first homogenous particle suspension for a period of time t, wherein some particles remain in the upper sub-column;
    (iv) mixing the particle suspension confined in the lower sub-column with a height h to prepare a second homogenous particle suspension;
    (v) measuring the particle concentration in the second homogenous particle suspension $X_2$; and
    (vi) determining the particle settling velocity v with the formula: $v=h(X_2-X_1)/tX_1$.

2. The method according to claim 1, in which the gravity settler comprises a column.

3. The method according to claim 1, in which particle settling velocity v ranges from about 0.1 cm/hr to about 100 cm/hr.

4. The method according to claim 1, in which particle settling velocity v ranges from about 0.5 cm/hr to about 60 cm/hr.

5. The method according to claim 1, in which particle settling velocity v ranges from about 1 cm/hr to about 10 cm/hr.

6. The method according to claim 1, in which the particles comprise spherical, regularly-shaped, or irregularly-shaped particles or cells.

7. The method according to claim 1, in which the particles comprise viable or nonviable cells.

8. The method according to claim 1, in which the particles comprise hybridoma cell lines.

9. The method according to claim 1, further comprising a step of measuring the settling velocity of polystyrene particles as standard particles.

10. The method according to claim 1, in which the first homogenous particle suspension comprises a suspension of monodisperse particles such as polystyrene particles.

11. The method according to claim 1, in which measuring the concentration of particles is performed with a Coulter Counter.

12. The method according to claim 11, in which the particles comprise polystyrene particles.

13. The method according to claim 1, in which measuring the concentration of particles is performed using a hemocytometer with a light microscope.

14. The method according to claim 13, in which the particles comprise cells.

15. The method according to claim 14, in which the cells comprise viable cells or nonviable cells.

16. The method according to claim 15, in which measuring the concentration of viable and nonviable cells is performed using the method of trypan blue exclusion.

17. A system for measuring particle settling velocity comprising:
  (i) a gravity settler such as a column;
  (ii) a separator;
  (iii) a means for measuring the particle concentration in a particle suspension;
  (iv) a timer; and
  (v) a leveled surface;
wherein the separator can vertically separate the column into an upper sub-column and a lower sub-column.

18. The system according to claim 17, in which the separator is a shutter.

19. An automatic system for measuring particle settling velocity comprising:
  (i) a gravity settler such as a column;
  (ii) a separator;
  (iii) a means for measuring the particle concentration in a particle suspension;
  (iv) a timer; and
  (v) a leveled surface;
wherein the separator can vertically separate the column into an upper sub-column and a lower sub-column.

20. The automatic system according to claim 19, further including a computational hardware such as a microprocessor, a computer processor, a digital signal processor, and a micro-controller.

* * * * *

UNITED STATES PATENT AND TRADEMARK OFFICE
CERTIFICATE OF CORRECTION

PATENT NO. : 8,667,832 B2  
APPLICATION NO. : 12/921267  
DATED : March 11, 2014  
INVENTOR(S) : Wang et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 549 days.

Signed and Sealed this
Eleventh Day of August, 2015

Michelle K. Lee
*Director of the United States Patent and Trademark Office*